United States Patent [19]

Hyer et al.

[11] 4,151,738
[45] May 1, 1979

[54] TOXIC GAS MONITOR HAVING AUTOMATIC CALIBRATION

[75] Inventors: Donald R. Hyer; John A. Roberts, both of Lynnfield, Mass.

[73] Assignee: General Electric Company, New York, N.Y.

[21] Appl. No.: 848,200

[22] Filed: Nov. 3, 1977

[51] Int. Cl.² ............................................. G01N 31/00
[52] U.S. Cl. ....................................................... 73/1 G
[58] Field of Search .................. 73/1 R, 1 G; 364/571

[56] References Cited

U.S. PATENT DOCUMENTS

| | | | |
|---|---|---|---|
| 3,441,863 | 4/1969 | Moriyaso | 330/9 |
| 3,504,521 | 4/1970 | Luckers | 73/1 |
| 3,516,002 | 6/1970 | Hillis | 300/51 |
| 4,032,856 | 6/1977 | Goldner | 330/69 |

*Primary Examiner*—S. Clement Swisher
*Attorney, Agent, or Firm*—R. G. Simkins; W. C. Bernkopf

[57] ABSTRACT

A gas monitor for monitoring the concentration of particular atmospheric constituent includes a sensor and a signal processor that provides concentration-indicating output signals in response to successive samples admitted to the sensor. The processor multiplies the sensor signals by a calibration signal. It automatically recalibrates the monitor by periodically causing a sample having a standard concentration to be admitted to the sensor and adjusting the calibration signal to provide a corresponding predetermined output signal level.

2 Claims, 2 Drawing Figures

TOXIC GAS MONITOR HAVING AUTOMATIC CALIBRATION

BACKGROUND OF THE INVENTION

This invention relates to a gas monitor that is used to measure the concentration of a particular constituent of a gaseous medium. More particularly it relates to a monitor that periodically recalibrates itself by measuring standard samples of known concentration and adjusting the monitor output accordingly.

Monitors of the type with which we are concerned are used to monitor selected areas for the concentrations of particular vapors or gases. For example, the workers in a manufacturing plant may be subjected to a toxic gas as the result of leakage from containers, pipes, or equipment in which the gas is used. A gas monitor is therefore installed to sense the atmospheric concentration of the gas in an area in which the leakage might occur and to sound an alarm when the concentration approaches a safe limit. A typical monitor comprises (a) a sensor which samples the atmosphere in the area under surveillance and provides an electrical signal corresponding to the atmospheric concentration of the toxic constituent, (b) a processor that processes the sensor signal and provides a corresponding output signal and (c) a indicator that converts the output signal to a visible or audible output.

The sensor used in a gas monitor is subject drift, i.e., changes in the correspondence between the sensor signals and the concentration of the monitored gaseous constituent. Accordingly, the monitor must be recalibrated periodically to maintain the accuracy of its output. In essence, calibration is accomplished by exposing the sensor to an atmosphere having a known concentration of the monitored constituent and adjusting the signal processor circuitry to make the monitor output correspond to that concentration. The procedure usually involves two standard concentrations. One of these is zero concentration and the other is a known finite concentration. In the instrument art the corresponding calibration adjustments are called "zero" and "span" adjustments.

The present invention is directed mainly to the span adjustment of a gas monitor. This adjustment has heretofore been made essentially by adjusting the setting of a potentiometer which controls the gain in an amplifier circuit. This is generally satisfactory for manual calibration, but where automatic calibration is desired, it requires the use of a servo motor to drive the potentiometer. This increases overall expense and makes for a more cumbersome device. Also, if the system is recalibrated often, as it should be for maintenance of accurate readings, reliability suffers because of wear in the potentiometer.

Accordingly, it is an object of this invention to provide a signal processor in the monitor that automatically accomplishes recalibration, including span adjustment, without the use of moving parts.

SUMMARY OF THE INVENTION

In a gas monitor incorporating our invention, the sensor signal is passed through an analog multiplier where it is multiplied by a span signal to provide the monitor output signal. Atmospheric samples are measured periodically under the control of a sequencer, and at predetermined intervals the sequencer initiates a recalibration cycle. Specifically, it causes a sample gas having a reference concentration of the monitored constituent to be applied to the sensor, and it also causes a recalibration circuit to switch on so as to change the span signal, as necessary, to make the output signal a correct indication of concentration. At the end of the recalibration cycle, the sequencer causes the system to return to sampling of the monitored atmosphere.

This invention is printed out with particularity in the appended claims. The above and further objects and advantages of this invention may be better understood by referring to the following description taken in conjunction with the accompanying drawings.

DESCRIPTION OF AN ILLUSTRATIVE EMBODIMENT

Figure 1:
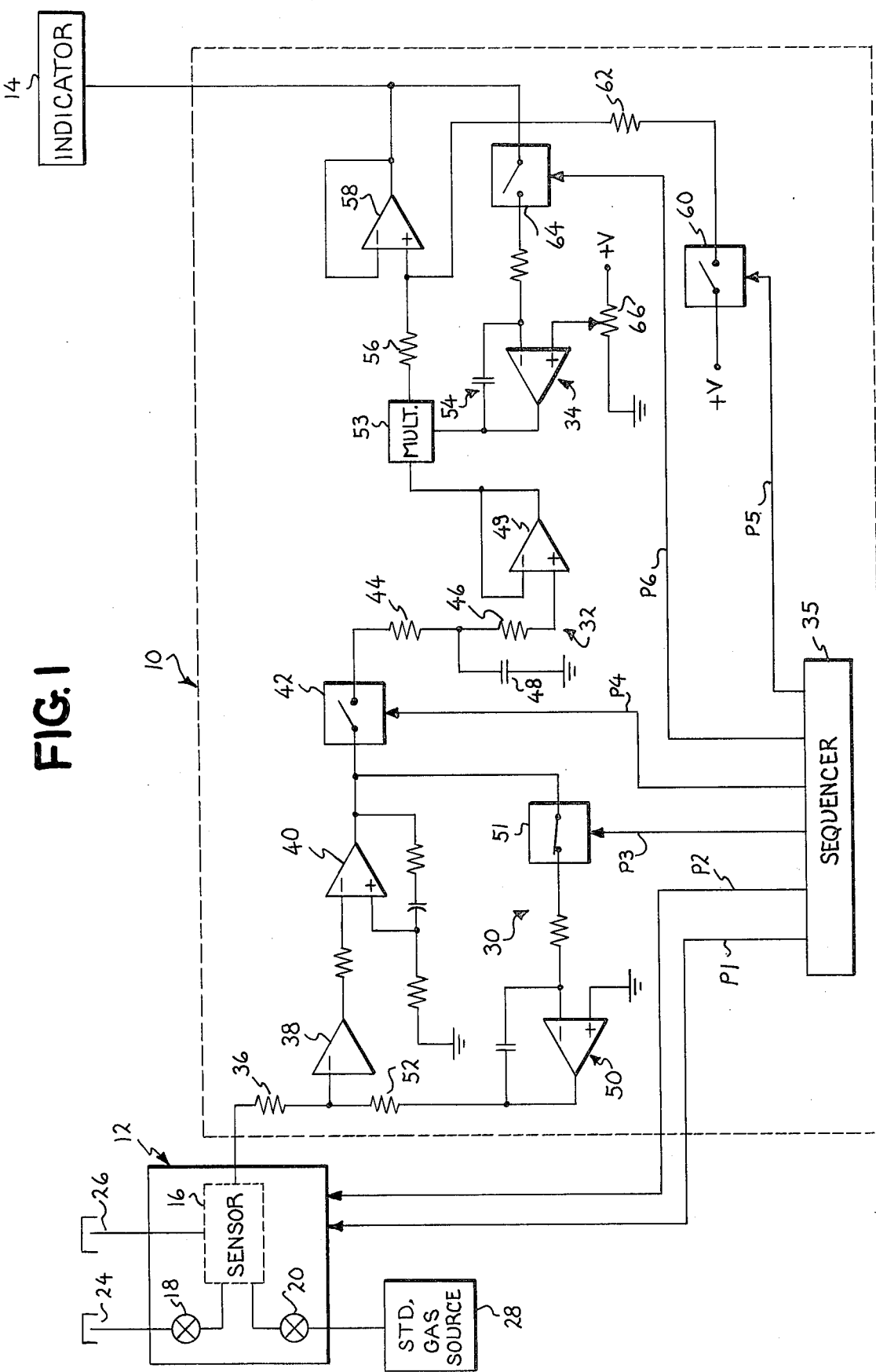
FIG. 1 is a block diagram of a system incorporating the present invention.

As shown in FIG. 1, a gas monitoring system incorporating the invention includes a signal processor, generally indicated at 10, connected to process the electrical output of a sensor unit 12 and provide a corresponding signal to an indicator 14, such as a strip chart recorder or the like.

The sensor unit 12 includes a sensor 16 capable of sensing the concentration of a monitored gaseous constituent down to levels of few part per million or less. The sensor 16 is connected by valves 18 and 20, respectively, to a sample inlet 24 and a standard gas source 28. The sample inlet 24 provides an atmospheric input to the sensor 16 form the area under surveillance by the system. A zero inlet 26 provides a sensor input from a gas having zero concentration of the monitored constituent. The standard gas source 28 provides an input flow having a known finite concentration of the monitored constituent. The valves 18 and 20 are solenoid-operated as described below to provide periodic measurement of atmospheric samples by way of the sample inlet 24 and, from time to time, calibration inputs from the standard gas source 28. As known, a pump is associated with the sensor 16 to draw gas continuously through the zero inlet 26 and from the inlet 24 and standard gas source 28 when the respective ones of the valves 18 and 20 are open.

The signal processor 10 includes a zero adjustment circuit 30, a sample-and-hold circuit 32 and a span adjustment circuit 34, all of which operate under control of a sequencer 35.

The signal from the sensor 16 is applied, by way of a summing resistor 36, to an amplifier 38 and then through an amplifier network 40 to a normally opened switch 42 controlled by the sequencer 35. When the switch 42 is closed, the signal is applied to the sample-and-hold circuit 32, which comprises series resistors 44 and 46, a shunt holding capacitor 48 and a unity gain amplifier 49.

The signal from the amplifier network 40 is also applied to an integrator 50 by way of a normally closed switch 51. The output of the integrator 50 is fed back to the amplifier 38, as described below, by way of a summing resistor 52.

The output of the amplifier 49 is also applied as one input of an analog multiplier 53 in the span adjustment circuit 34. The other input of the multiplier 53 is a span signal provided by a span integrator 54. The output of the multiplier 53 is applied through a summing resistor 56 to a unity gain amplifier 58. The output of the amplifier 58, in turn, is connected to the output indicator 14.

Figure 2:
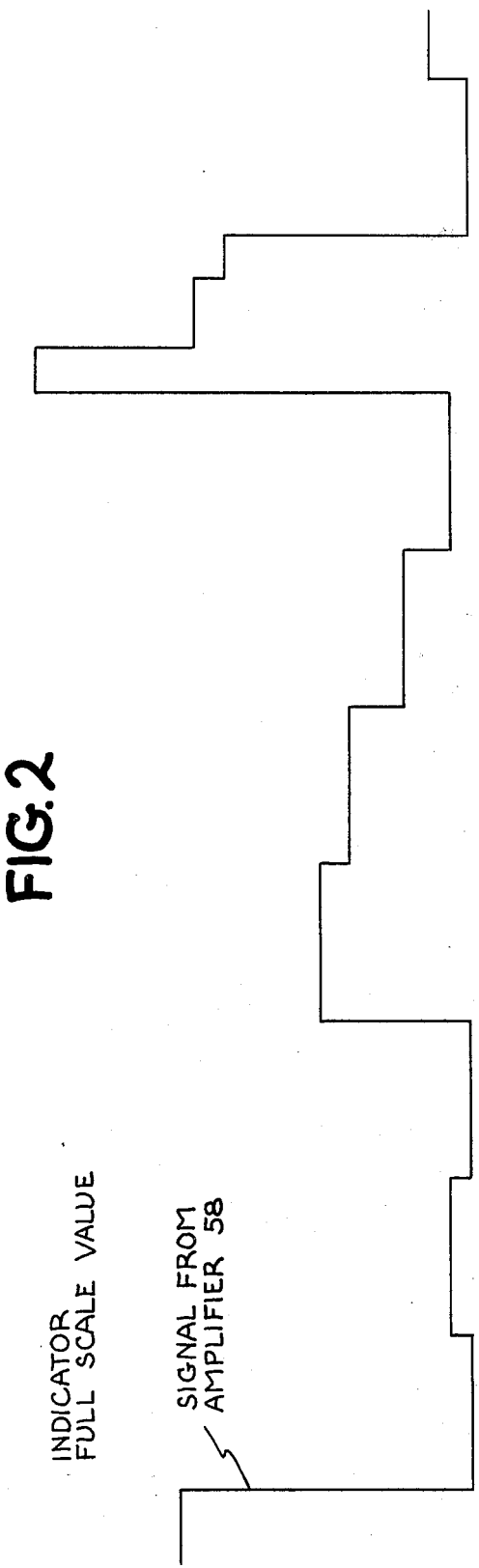
FIG. 2 is a timing diagram of the sampling and recalibration cycles of the system.
Figure 2:
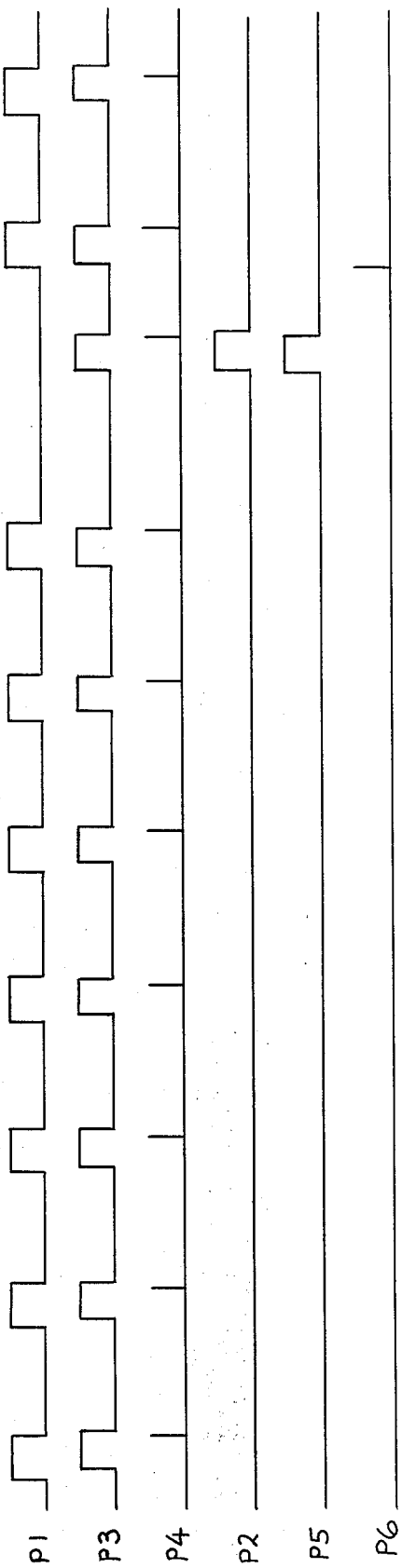

As discussed above, the sensor 16 is subject to drift and, therefore, must be recalibrated periodically. Calibration requires both zero and span adjustments of the signal processor 10. The manner in which the system automatically makes these adjustments will now be described in detail with reference to FIGS. 1 and 2.

Operation of the monitor is controlled by the sequencer 35. Sequencers are well known and there is therefore no need to describe the circuitry of the sequencer 35. Rather it is sufficient to know when the various control signals are emitted by the sequencer.

Considering first the normal sample measurement cycle of the monitor, the sequencer 35 as described later, disconnects the integrating amplifier 50 from the amplifier network 40. It also emits a P1 pulse which opens the valve 18 for a sufficient period of time, e.g. 20 seconds, to expose the sensor 16 a new sample from the atmosphere under surveillance. Toward the end of the P1 pulse, a P4 pulse closes the switch 42 for a short period of time so that by the time the P1 pulse terminates, the capacitor 48 is charged to a voltage corresponding to the concentration of the monitored gas in the sample that has been admitted to the sensor 16 The valve 18 then closes and the switch 42 opens so that the capacitor 48 retains its charge and the output of the sample and hold circuit 32 remains at the capacitor voltage. The multiplier 53 multiplies that voltage by the span voltage from the integrator 54 and thereby provide an output signal to the indicator 14 that is a measure of the concentration of the monitored gaseous constituent.

After a predetermined time, e.g. two to ten minutes, the P1 pulse is again emitted by the sequencer 35 to admit another sample to the sensor 16 and a P4 pulse is emitted to provide a corresponding output to the indicator 14. This sample measurement cycle repeats for a predetermined number of samples, at which time the sequencer initiates the calibration operation thereby to provide automatic span adjustment.

Specifically, the sequencer emits a P5 marker pulse of short duration, e.g. 5 seconds, to a switch 60 that applies a relatively high voltage through a summing resistor 62 to the amplifier 58. This causes the output indicator 14 to register a marker whose amplitude is sufficient to inform the user that the calibration operation is underway.

The processor 10 is always performing a zero adjustment except during a sampling or calibration operation. As previously indicated, the sequencer 35 samples the gas periodically (e.g., 20 seconds each two through 10 minutes). During the remaining interval, the switch 51 is closed and the sensor 16 receives only filtered air through the inlet 26. Thus, the air is considered to have a zero concentration of the gas being sampled. If the output signal from the sensor drifts during this interval, the output signal from the amplifying network 40 causes the integrator output to provide a compensating input signal to the input summing junction of the amplifier 38. That is, the output of the integrator increases or decreases until it cancels the output of the sensor 16 at the input terminals of the amplifier 38 and thus reduces the output of the filter 40 to zero. This completes the zero point adjustment.

When the sequencer 35 initiates a sampling or calibration operation, the sequencer generates a P3 pulse. The leading edge of this pulse is delayed slightly from the leading edge of the corresponding P1 or P2 pulse, and it opens the switch 51 for the duration of that operation. As a result, the output signal from the integrator 50 remains constant during that operation. The drift in the output signal, however, is relatively slow, so it can be assumed that no further drift occurs during the sampling or calibration operation. Upon completion of the operation, the respective one of the P1 or P2 pulses terminates. The switch 51 then closes, and the integrator 50 thereby is enabled to provide zero compensation again.

The sequencer then emits a P2 pulse to open the valve 20 to apply to the sensor 16 a calibration sample consisting of a known concentration of the toxic gas from the standard gas source 28. Toward the end of the P2 pulse, a P4 pulse momentarily closes the switch 42 so that the capacitor 48 charges to a voltage corresponding to the output of the sensor 16. As a result the indicator 14 registers an output showing response of the monitor to the standard concentration prior to span adjustment. This indicates to the user the amount of span drift in the monitor between span adjustments.

Finally, for span adjustment, the sequencer emits a short P6 pulse to close a switch 64 so that the integrator 54 commences to integrate the output of the amplifier 58. The output of the integrator, i.e., the span input to the multiplier 53, changes until the output of the amplifier 58 equals the voltage from a potentiometer 66. The potentiometer has initially been set manually so that its output is a voltage that provides a reading on the indicator 14 corresponding to the standard concentration of the monitored constituent used in calibrating the system. Thus, during span adjustment the output of the integrator 54 changes as required to force the output of the amplifier 58 to this voltage and thus provide a reading n the indicator 14 that indicates the standard concentration.

After the P6 pulse, the sequencer 35 commences another series of P1, P3 and P4 pulses and corresponding sample measurement cycles, after which the recalibration process is again initiated.

From the foregoing, it will be apparent that recalibration is not only automatic, it is accomplished without any moving parts in the signal processor. The processor therefore can be a small, relatively inexpensive unit. Moreover, since the problems associated with moving calibration devices, such as potentiometers, are eliminated, the processor has a highly reliable operation.

What we claim and desire to secure by Letters Patent of the United States is:

1. An automatically calibrated system for monitoring the concentration of constituent of an atmosphere, said system comprising:
   A. a sensor that provides an electrical sensor signal in response to the concentration of said constituent in a sample admitted to said sensor,
   B. sample means for admitting samples of said atmosphere to said sensor in response to a sample activation signal,
   C. standard sample means for admitting to said sensor samples having a predetermined concentration of said constituent,
   D. signal processing means providing an output signal in response to said sensor signal, said processing means including:
      i. a sample-and-hold circuit, which, when activated, samples and holds said sensor signal, ii. a multiplier for multiplying the output of said sample-and-hold circuit by a calibration signal to provide said output signal, iii. calibration means for developing said calibration signal, said calibration means including means for adjusting said calibration signal to provide an output signal having a predetermined level and means for holding said calibration signal after said adjustment, and iv. sequence means connected to:
  a. initiate a series of sample measurement cycles by activating said sample means and said sample-and-hold means, and
  b. periodically actuate said calibration means to recalibrate said processor by activating said standard sample means and said sample-and-hold means to provide a signal responsive to said predetermined concentration, and activating said calibration signal adjustment means to make said output signal have said predetermined level in response to said predetermined concentration.

2. The system defined in claim 1 wherein said sensor receives a gas having zero concentration of said constituent at times other than the sample measurement cycles and said system further includes zero adjustment means connected to add to said sensor signal a zero adjustment signal, said zero adjustment means including:

i. an integrator for generating said zero adjustment signal, and ii. means connected to said sequencing means for coupling to said integrator the sum of said sensor signal and said zero adjustment signal, said integrator integrating the sum until the sum is zero, the sum being the input signal for said sample-and-hold means.

* * * * *